(12) United States Patent
Wöldike et al.

(10) Patent No.: US 7,858,747 B2
(45) Date of Patent: Dec. 28, 2010

(54) **EXPRESSION OF PROTEINS IN *E.COLI***

(75) Inventors: Helle Fabricius Wöldike, Lynge (DK); Christine Bruun Schiødt, Bronshoj (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/064,837

(22) PCT Filed: Aug. 30, 2006

(86) PCT No.: PCT/EP2006/065817

§ 371 (c)(1),
(2), (4) Date: Aug. 5, 2008

(87) PCT Pub. No.: WO2007/025987

PCT Pub. Date: Mar. 8, 2007

(65) Prior Publication Data

US 2009/0035821 A1    Feb. 5, 2009

Related U.S. Application Data

(60) Provisional application No. 60/715,304, filed on Sep. 8, 2005.

(30) Foreign Application Priority Data

Aug. 30, 2005  (EP)  .................. 05107918

(51) Int. Cl.
*C07K 1/00*  (2006.01)

(52) U.S. Cl. ..................................... 530/350

(58) Field of Classification Search .................. 530/350
See application file for complete search history.

(56) References Cited

U.S. PATENT DOCUMENTS 5,284,933 A       2/1994  Dobeli et al.
7,250,274 B2 *    7/2007  Chan et al. .................. 435/69.5

FOREIGN PATENT DOCUMENTS

| WO | WO 98/24816   | * | 6/1998  |
|----|---------------|---|---------|
| WO | WO 03/027122  |   | 4/2003  |
| WO | WO 04/000220  |   | 12/2003 |
| WO | WO 2004/055168 |  | 7/2004  |
| WO | WO 2006/062685 |  | 6/2006  |
| WO | WO 2007/025987 |  | 3/2007  |

OTHER PUBLICATIONS

Gaberc-Porekar et al., "Histidine in Affinity Tags and Surface Clusters for Immobilized Metal-Ion Affinity Chromatography of Trimeric Tumor Necrosis Factor Alpha," Journal of Chromatography 1999, vol. 852, pp. 177-128.

Razeghifard, Reza, "On-Column Refolding of Recombinant Human Interleukin-4 From Inclusion Bodies," Protein Expression and Purification 2004, vol. 37, pp. 180-186.

Zhou, C. Z. et al., "Developments in Structural Genomics: Protein Purification and Function Interpretation", Current Genomics, 2004, vol. 5, pp. 37-48.

* cited by examiner

*Primary Examiner*—Maryam Monshipouri
(74) *Attorney, Agent, or Firm*—Reza Green; Teresa Chen (57) ABSTRACT

Plasmid comprising a DNA tag encoding a peptide tag of the sequence $MX_1(X_2X_3)_n$ wherein $X_1$ represents K, R or H; $X_2$ represents A, G, H, M, S or T; $X_3$ represents K, R, H, A, Q or V; n represents an integer of 1 or larger; and wherein said DNA is operably-linked to a promoter sequence are provided.

4 Claims, 2 Drawing Sheets

SEQUENCE LISTING

<160> NUMBER OF SEQ ID NOS: 27

<210> SEQ ID NO 1
<211> LENGTH: 423
<212> TYPE: DNA
<213> ORGANISM: Homo sapiens

<400> SEQUENCE: 1

```
catatgcaag gtcaagatcg ccacatgatt agaatgcgtc aacttataga tattgttgat      60
cagctgaaaa attatgtgaa tgacctggtt ccggaattcc tgccggctcc ggaagatgtt     120
gagaccaact gtgagtggtc cgctttctcc tgtttccaga aagcccagct gaaatccgca     180
aacaccggta acaacgaacg tatcatcaac gtttccatta aaaaactgaa acgtaaaccg     240
ccgtccacca acgcaggtcg tcgtcagaaa caccgtctga cctgcccgtc ctgtgattct     300
tatgagaaaa aaccgccgaa agaattcctg gaacgtttca aatccctgct gcagaaaatg     360
attcaccagc acctgtcctc tcgtacccac ggttccgaag attcctgatg atttggcgga     420
tcc                                                                    423
```

<210> SEQ ID NO 2
<211> LENGTH: 134
<212> TYPE: PRT
<213> ORGANISM: Homo sapiens

<400> SEQUENCE: 2

```
Met Gln Gly Gln Asp Arg His Met Ile Arg Met Arg Gln Leu Ile Asp
1               5                   10                  15

Ile Val Asp Gln Leu Lys Asn Tyr Val Asn Asp Leu Val Pro Glu Phe
            20                  25                  30

Leu Pro Ala Pro Glu Asp Val Glu Thr Asn Cys Glu Trp Ser Ala Phe
        35                  40                  45

Ser Cys Phe Gln Lys Ala Gln Leu Lys Ser Ala Asn Thr Gly Asn Asn
    50                  55                  60

Glu Arg Ile Ile Asn Val Ser Ile Lys Lys Leu Lys Arg Lys Pro Pro
65                  70                  75                  80
```

Ser Thr Asn Ala Gly Arg Arg Gln Lys His Arg Leu Thr Cys Pro Ser
                85                  90                  95

Cys Asp Ser Tyr Glu Lys Lys Pro Pro Lys Glu Phe Leu Glu Arg Phe
            100                 105                 110

Lys Ser Leu Leu Gln Lys Met Ile His Gln His Leu Ser Ser Arg Thr
        115                 120                 125

His Gly Ser Glu Asp Ser
        130

<210> SEQ ID NO 3
<211> LENGTH: 418
<212> TYPE: DNA
<213> ORGANISM: Homo sapiens

<400> SEQUENCE: 3
ccaaggtcaa gatcgccaca tgattagaat gcgtcaactt atagatattg ttgatcagct      60
gaaaaattat gtgaatgacc tggttccgga attcctgccg gctccggaag atgttgagac     120
caactgtgag tggtccgctt tctcctgttt ccagaaagcc cagctgaaat ccgcaaacac     180
cggtaacaac gaacgtatca tcaacgtttc cattaaaaaa ctgaaacgta aaccgccgtc     240
caccaacgca ggtcgtcgtc agaaacaccg tctgacctgc cgtcctgtga ttcttatga     300 gaaaaaaccg ccgaaagaat tcctggaacg tttcaaatcc ctgctgcaga aaatgattca     360
ccagcacctg tcctctcgta cccacggttc cgaagattcc tgatgatttg cggatcc        418

<210> SEQ ID NO 4
<211> LENGTH: 405
<212> TYPE: DNA
<213> ORGANISM: Homo sapiens

<400> SEQUENCE: 4
caaggtcaag atcgccacat gattagaatg cgtcaactta tagatattgt tgatcagctg      60
aaaaattatg tgaatgacct ggttccggaa ttcctgccgg ctccggaaga tgttgagacc     120
aactgtgagt ggtccgcttt ctcctgtttc agaaagccc agctgaaatc cgcaaacacc      180
ggtaacaacg aacgtatcat caacgtttcc attaaaaaac tgaaacgtaa accgccgtcc     240
accaacgcag gtcgtcgtca gaaacaccgt ctgacctgcc gtcctgtga ttcttatgag      300 aaaaaaccgc cgaaagaatt cctggaacgt ttcaaatccc tgctgcagaa aatgattcac     360
cagcacctgt cctctcgtac ccacggttcc gaagattcct gatga                     405

<210> SEQ ID NO 5
<211> LENGTH: 133
<212> TYPE: PRT
<213> ORGANISM: Homo sapiens

<400> SEQUENCE: 5

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

```
Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Met His Ala His
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Met His Ala His
1

<210> SEQ ID NO 8
<211> LENGTH: 4
<212> TYPE: PRT
<213> ORGANISM: Artificial Sequence
<220> FEATURE:
<223> OTHER INFORMATION: Synthetic

<400> SEQUENCE: 8

Met His His Ala
1

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Met His His Gln
1

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Met His His Val
1
```

-continued

```
<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Met Lys His Lys
1

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Met Lys Ala Lys
1

<210> SEQ ID NO 13
<211> LENGTH: 4
<212> TYPE: PRT
<213> ORGANISM: Artificial Sequence
<220> FEATURE:
<223> OTHER INFORMATION: Synthetic

<400> SEQUENCE: 13

Met Arg Ala Arg
1

<210> SEQ ID NO 14
<211> LENGTH: 4
<212> TYPE: PRT
<213> ORGANISM: Artificial Sequence
<220> FEATURE:
<223> OTHER INFORMATION: Synthetic

<400> SEQUENCE: 14

Met Lys Met Lys
1

<210> SEQ ID NO 15
<211> LENGTH: 4
<212> TYPE: PRT
<213> ORGANISM: Artificial Sequence
<220> FEATURE:
<223> OTHER INFORMATION: Synthetic

<400> SEQUENCE: 15

Met Lys Ser Lys
1

<210> SEQ ID NO 16
<211> LENGTH: 4
<212> TYPE: PRT
<213> ORGANISM: Artificial Sequence
<220> FEATURE:
<223> OTHER INFORMATION: Synthetic

<400> SEQUENCE: 16

Met Lys Thr Lys
1

<210> SEQ ID NO 17
```

```
<211> LENGTH: 13
<212> TYPE: DNA
<213> ORGANISM: Artificial Sequence
<220> FEATURE:
<223> OTHER INFORMATION: Synthetic

<400> SEQUENCE: 17
tatgcatgcg cat                                                         13

<210> SEQ ID NO 18
<211> LENGTH: 13
<212> TYPE: DNA
<213> ORGANISM: Artificial Sequence
<220> FEATURE:
<223> OTHER INFORMATION: Synthetic

<400> SEQUENCE: 18
tatgcacgct cac                                                         13

<210> SEQ ID NO 19
<211> LENGTH: 13
<212> TYPE: DNA
<213> ORGANISM: Artificial Sequence
<220> FEATURE:
<223> OTHER INFORMATION: Synthetic

<400> SEQUENCE: 19
tatgcatcac gcg                                                         13

<210> SEQ ID NO 20
<211> LENGTH: 13
<212> TYPE: DNA
<213> ORGANISM: Artificial Sequence
<220> FEATURE:
<223> OTHER INFORMATION: Synthetic

<400> SEQUENCE: 20
tatgcatcac cag                                                         13

<210> SEQ ID NO 21
<211> LENGTH: 13
<212> TYPE: DNA
<213> ORGANISM: Artificial Sequence
<220> FEATURE:
<223> OTHER INFORMATION: Synthetic

<400> SEQUENCE: 21
tatgcatcac gtg                                                         13

<210> SEQ ID NO 22
<211> LENGTH: 13
<212> TYPE: DNA
<213> ORGANISM: Artificial Sequence
<220> FEATURE:
<223> OTHER INFORMATION: Synthetic

<400> SEQUENCE: 22
tatgaaacac aaa                                                         13

<210> SEQ ID NO 23
<211> LENGTH: 13
<212> TYPE: DNA
<213> ORGANISM: Artificial Sequence
<220> FEATURE:
<223> OTHER INFORMATION: Synthetic

<400> SEQUENCE: 23
```

```
tatgaaagcg aaa                                                              13

<210> SEQ ID NO 24
<211> LENGTH: 13
<212> TYPE: DNA
<213> ORGANISM: Artificial Sequence
<220> FEATURE:
<223> OTHER INFORMATION: Synthetic

<400> SEQUENCE: 24
tatgcgtgcg cgt                                                              13

<210> SEQ ID NO 25
<211> LENGTH: 13
<212> TYPE: DNA
<213> ORGANISM: Artificial Sequence
<220> FEATURE:
<223> OTHER INFORMATION: Synthetic

<400> SEQUENCE: 25
tatgaaaatg aaa                                                              13

<210> SEQ ID NO 26
<211> LENGTH: 13
<212> TYPE: DNA
<213> ORGANISM: Artificial Sequence
<220> FEATURE:
<223> OTHER INFORMATION: Synthetic

<400> SEQUENCE: 26
tatgaaaagc aaa                                                              13

<210> SEQ ID NO 27
<211> LENGTH: 13
<212> TYPE: DNA
<213> ORGANISM: Artificial Sequence
<220> FEATURE:
<223> OTHER INFORMATION: Synthetic

<400> SEQUENCE: 27
tatgaaaacc aaa                                                              13
```

EXPRESSION OF PROTEINS IN *E.COLI*

CROSS-REFERENCE TO RELATED APPLICATIONS

This application is a 35 U.S.C. §371 national stage application of International Patent Application PCT/EP2006/065817 (published as WO 2007/025987), filed Aug. 30, 2006, which claimed priority of European Patent Application 05107918.4, filed Aug. 30, 2005; this application further claims priority under 35 U.S.C. §119 of U.S. Provisional Application 60/715,304, filed Sep. 8, 2005.

BACKGROUND OF THE INVENTION

Recombinant protein expression systems facilitate the production of protein, polypeptides and peptides for screening in drug discovery and for a wide range of applications including vaccine production. Bacterial expression systems have been the main method of choice, largely due to the ease of cloning genes in bacteria, although yeast and baculovirus provide reliable alternative expression systems.

Despite the wide use of recombinant expression systems for the production of proteins, available methods cannot be relied upon to produce any given protein in sufficient yields and having sufficient homogeneity to meet downstream requirements. Protein yield can be a major problem associated with the over-expression of proteins in bacteria, where the protein is directly toxic for the host cell, or where its accumulation disrupts host cell metabolism or growth. Large proteins, as well as proteins with a complex secondary and tertiary structure, tend to be insoluble and accumulate in inclusion bodies in the host cell, where they are generally better tolerated by the host. However, smaller proteins tend to be soluble and their accumulation may be toxic. A number of vectors systems are designed to express the target recombinant protein as a fusion protein with a short or longer N-terminal peptide tag. Such tags, such as the histidine-, or maltose binding-tag are particularly useful for the subsequent purification of the recombinant proteins. There remains however a need for an efficient expression system, especially for therapeutic proteins that are potentially toxic and difficult to express.

SUMMARY OF THE INVENTION

The invention provides a self-replicating DNA plasmid for recombinant expression of an N-terminally tagged protein in a microbial host cell comprising a DNA tag having a nucleotide sequence encoding a peptide tag of formula [I]

$$MX_1(X_2X_3)_n \quad [I]$$

wherein
$X_1$ represents K, R or H;
$X_2$ represents A, G, H, M, S or T;
$X_3$ represents K, R, H, A, Q or V;
n represents an integer of 1 or larger;
and wherein said DNA is operably-linked to a promoter sequence.

Furthermore, the plasmid of the invention may further comprise a nucleic acid sequence encoding a protein fused in-frame with said DNA tag for recombinant expression of an N-terminally tagged protein encoded by said nucleic acid fused to said DNA tag.

The invention provides a microbial host cell comprising the DNA plasmid of the invention.

In a further embodiment of the invention provides a tagged protein comprising an N-terminal peptide tag fused to a protein, wherein said tag has a sequence according to formula I.

A method for recombinant expression of an N-terminally tagged protein in a microbial host cell comprising the steps of constructing a recombinant plasmid comprising inserting a DNA sequence encoding a protein in-frame and 3' to the DNA tag of the plasmid according to the present invention, and introducing said recombinant plasmid into a host microbial cell, and inducing expression of said N-terminally tagged protein in a microbial host cell.

DESCRIPTION OF THE DRAWINGS

Panel A shows the Maldi spectrum of fractions prior to tag removal

Panel B shows the same fractions after tag removal.

ABBREVIATIONS

Amino acid: Alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W), tyrosine (Y); valine (V).
C-terminal: carboxy (C)-terminal part of a protein, comprising one or more amino acid residues.
hIL-21: human interleukin-21
N-terminal: amino (N)-terminal part of a protein, comprising one or more amino acid residues.
SDS PAGE: sodium dodecyl (lauryl) sulfate-polyacrylamide gel

DESCRIPTION OF THE INVENTION

The present invention provides a DNA tag, an expression-vector or -plasmid suitable for the recombinant expression of a heterologous protein, and a method for recombinant protein expression, which are compatible with the subsequent purification of the recombinant protein, and eventual processing of the recombinant protein to recover the protein in its native and active form.

As used herein, the term "DNA tag" is defined as a DNA molecule encoding an N-terminal protein tag that is added to a DNA sequence coding for a heterologous protein, and whose in frame expression in a micro-organism produces a tagged protein or fusion protein. The DNA tag of the present invention codes for at least four amino acids having an amino acid sequence defined by formula I.

In one embodiment, n is 1.
In one embodiment, $X_1$ represents H or K.
In one embodiment, $X_2$ represents A, H, M, S or T.
In one embodiment, the DNA tag of the present invention codes for an amino acid sequence selected from the list given in Table 1, with a SEQ ID Nos: 6-16. As illustrated in Example 1, the expression of a DNA sequence comprising a DNA tag of the invention, fused in-frame to the coding sequence of a protein, facilitates significantly higher levels of expression of the protein than a control sequence encoding the protein fused to an N-terminal methionine. In one embodiment, the DNA tag of the invention encodes an amino acid sequence selected from among MHAH, MHHA, MHHV, MKHK, MKMK, MKSK, and MKTK, with respectively SEQ ID Nos: 7, 8,10, 11, 14, 15 and 16. In one embodiment, the DNA tag of the invention encodes the amino acid sequence MKSK [SEQ ID No: 15]. While not wishing to be bound by theory, it is believed that recombinant protein expression in a host microbial cell, in particular an *E. coli* cell, is enhanced if the expressed protein accumulates in a form that is non-toxic to host cell metabolism or growth, for example in an inclusion body. Thus the selected N-terminal protein tags fused to recombinant proteins may enhance their expression by facilitating their accumulation in inclusion bodies.

Many mammalian proteins of interest are secreted in their natural host and synthesized with a signal peptide, which is cleaved off during secretion. The N-terminal of the secreted, mature protein therefore in most cases begins with an amino acid different from methionine, the natural N-terminal of all de novo synthesized proteins, including heterologous, intracellularly accumulated proteins in *E. coli*. To avoid uncertainties about cleavage of the N-terminal methionine, the addition of a small peptide tag as described, with known in vitro cleavage properties, is highly advantageous in obtaining the mature protein of interest.

The DNA tag provided by the present invention may be added to a DNA sequence encoding a protein for the purposes of its recombinant expression in a host microbial cell, in particular a bacterial cell. The DNA tag has application in the recombinant expression of a wide number of useful proteins in a host microbial cell, in particular for the expression of therapeutic proteins, for example human growth hormone, IL-20, IL-21, and GLP-1. The DNA tag encoding the N-terminal peptide tag is fused in-frame with the DNA sequence encoding the protein to be expressed, such that the expression product obtainable in a host cell is a tagged- or fusion-protein. If the DNA tag encodes an N-terminal peptide tag that is more that four amino acids, the peptide tag is preferably extended by the addition of dipeptides, whose amino acid composition is compatible with their cleavage by a diaminopeptidase, such as dipeptidyl amino peptidase I. Dipeptides that are compatible with cleavage by a diaminopeptidase include any pair of the amino acids found in positions 1+2 or 3+4 of the peptide tag sequences listed in Table 1. For example, suitable dipeptides found in the tag encoded by construct DAP14 are MH and AH. The expressed tagged- or fusion-protein may comprise the peptide tag fused directly to the first amino acid of the mature protein to be expressed, such that cleavage of the peptide tag with the removal of dipeptides releases the expressed protein in its mature form. In the event that the peptide tag of the expressed tagged- or fusion-protein is to be removed by an aminopeptidase, it is desirable to ensure that the amino acid sequence of the mature form of the expressed protein starts with, or is preceded by, a residue that can function as a stop point beyond which the aminopeptidase can not continue. In this manner the mature form of the expressed protein is protected from N-terminal proteolytic cleavage. A suitable amino acid residue that can act as a stop point for a diaminopeptidase may be selected from Q, P, R, K. The amino acid residue Q can be used as the stop point, by virtue of its ability to form pyroglutamate in the presence of glutamate cylcotransferase. In the event that the N-terminal amino acid of the mature protein is not itself a residue that can function as a stop, it is desirable to extend the DNA tag by one codon encoding a suitable stop residue, which is then fused to the DNA sequence encoding the desired mature protein. A preferred stop residue to be added to the end of the peptide tag is Q, since this residue can be removed from the N-terminus of the expressed protein with pyroglutamyl aminopeptidase, following dipeptidyl aminopeptidase cleavage of the peptide tag.

The DNA tag of the invention when fused in-frame to the coding sequence of a protein to be recombinantly expressed, provides a tagged-protein whose peptide tag has a predominance of charged polar side chains. The presence of additional charged residues in the tagged protein may be particularly useful in subsequent purification steps that discriminate on the basis of protein mass charge.

A further embodiment of the invention provides a DNA molecule comprising a DNA tag, encoding a peptide tag according to any one listed in Table 1 having SEQ ID Nos: 6-16, fused in-frame to a DNA sequence encoding interleukin 21 (hIL-21) having SEQ ID Nos: 4, as described in Example 1. In one embodiment the DNA tag, fused in-frame to a DNA sequence encoding hIL-21, is one that encodes an amino acid sequence selected from among MHAH, MHHA, MHHV, MKHK, MKMK, MKSK, and MKTK; in a further embodiment, the DNA tag encodes the amino acid sequence MKSK.

In one embodiment of the invention the DNA tag has the nucleotide sequence of construct DAP 14, 25, 15, 16, 22, 17, 18, 19, 21, 23 and 24 listed in Table 1, corresponding to SEQ ID Nos: 17-27, respectively. A DNA tag having any one of these nucleotide sequences may be fused in-frame to a DNA sequence encoding hIL-21. In one example of the invention the DNA tag, corresponding to any one of SEQ ID Nos: 17-27 is fused in-frame to a DNA molecule encoding hIL-21 having the nucleotide sequence of SEQ ID No: 4. It should be understood that the sequences with SEQ ID Nos: 17-27 are shown with an adaptation to insertion into an Nde1-Sty1 environment. Other restriction sites may be chosen, and it lies within the capabilities of a person skilled in the art to adjust the sequences accordingly.

In one aspect, the invention provides an expression-vector or -plasmid comprising a DNA tag encoding the peptide tag of the invention. The DNA tag may be inserted adjacent to, or in, a suitable cloning site of the vector or plasmid, such that the tag is located downstream and operably-linked to a promoter sequence. Preferably the DNA tag is flanked by a restriction-enzyme cleavage site that facilitates the downstream in-frame insertion of a DNA sequence encoding the protein to be recombinantly expressed. One skilled in the art will readily recognise suitable preferred flanking sequences to facilitate downstream in-frame cloning of the coding sequence of a desired protein. A promoter sequence in the plasmid or vector of the invention, that is operably-linked to the DNA-tag of the invention, has a nucleotide sequence that is capable of directing transcription of the DNA molecule encoding the tagged protein in the selected host microbial cell. Promoter sequences, suitable for recombinant protein expression in bacteria and in particular in *E. coli,* are well known to one skilled in the art, but include any one of the T7, trc, lac and tac promoters. A preferred vector incorporating the expression cassette comprising a promoter operably-linked to the DNA-tag of the invention is one that is self-replicating and has a selectable maker, for example ampicillin.

In one embodiment, the expression-vector or -plasmid of the invention further comprises a DNA sequence encoding a protein to be recombinantly expressed, where the DNA sequence is cloned downstream and in-frame with said DNA tag. In one example, the DNA sequence cloned in the expression plasmid is one that encodes hIL-21 that is capable of expression as a tagged protein when the expression plasmid is introduced into a suitable host cell. The DNA sequence encoding hIL-21 in the expression-vector or -plasmid of the invention may have the nucleotide sequence of SEQ ID No: 4.

A host cell, to be transformed with the expression-plasmid-vector of the invention, that is suitable for the expression of a tagged protein, is well-known to one skilled in the art. A preferred bacterial host stain is a derivative strain of *E. coli* B, for example the protease-deficient strain *E. coli* BL21 (DE3) habouring the T7 polymerase gene on the chromosome.

The present invention, further provides a tagged protein comprising an N-terminal peptide tag fused to a protein, wherein the peptide tag has a sequence as defined by formula I. In one embodiment, said peptide tag has at least four amino acids having an amino acid sequence selected from the list given in Table 1, more preferably an amino acid sequence selected from among MHAH, MHHA, MHHV, MKHK, MKMK, MKSK, and MKTK, and most preferably the amino acid sequence MKSK. In one embodiment the tagged protein comprises a peptide tag fused to the protein hIL-21, wherein said hIL-21 protein has the amino acid sequence SEQ ID No: 5. The tagged protein according to the present invention can be obtained by recombinant expression of the expression-plasmid or -vector of the present invention. The tagged protein may be subjected to purification steps, and/or one or more proteolytic processing steps described herein for the removal of the peptide tag from the tagged protein in order to provide a mature protein having one or more applications.

The invention further provides a method for recombinant expression in a host microbial cell of a tagged protein encoded by a DNA tag of the invention fused in-frame to a coding sequence, whereby the fused DNA sequence encodes said tagged protein, in order to improve the yield of the expressed target protein. Accordingly, the method includes the steps of constructing an expression-plasmid or -vector coding for a fusion protein which comprises an N-terminal peptide tag fused to a protein, whereby the coding sequence is terminated by a stop codon. Expression of the tagged protein is directed by a promoter operably-linked to the coding sequence of the tagged protein, whereby the promoter is one that is recognised by the expression system of the host cell. According to one embodiment of the invention, the construction of an expression-vector for the expression of hIL-21 is described in example 1.

The expression-vector or -plasmid of the invention is transfected into a host microbial cell, preferably the bacterium *E. coli,* and host cells transformed by the vector are identified, isolated and cultivated under conditions compatible with multiplication of the host cell and the expression of the tagged protein.

Expression of the tagged protein of the invention in a host microbial cell is preferably inducible. For example, where the host cell is an *E. coli* strain, and expression is regulated by the lac operator, expression may be induced by addition of about 0.5-1 mM isopropyl β-D-thiogalactopyranoside (IPTG) that de-represses the lac promoter. After a suitable induction by IPTG, for example for 3-4 hours, the host cells may be lysed, for example by sonication or freeze-thaw procedures, and the cell lysate separated into soluble and insoluble fractions by centrifugation. The tagged protein, depending on its solubility, may be located in the soluble fraction, or more preferably in inclusion bodies that fractionate with the cell pellet.

When the tagged protein is located in inclusion bodies, a solubilisation and refolding step may be required prior to its further purification, employing conditions optimized for the tagged protein according to protocols well known in the art. A wide variety of protein separation and purification protocols may be employed to achieve the required degree of purification. Methods for determining the purity of the purified tagged protein of the invention and the subsequently derived mature protein are well known in the art, and are illustrated in Example 2.

Removal of the peptide tag from the tagged protein of the invention may employ di-peptidyl aminopeptidase, which may be combined with glutamine cyclotransferase if the stop residue is Q. Removal of the tag may be performed either before or after purification of the recombinantly expressed protein of the invention.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

In summary, the present invention provides an expression-vector or -plasmid comprising a DNA tag encoding a peptide tag, that is operably-linked to a promoter capable of directing expression in a host microbial cell of said DNA tag and any protein coding sequence fused in-frame with said DNA tag. The particular advantage of employing the expression-vector or -plasmid of the invention for recombinant protein expression of a protein coding sequence fused in-frame with said DNA tag is that the expression levels in a host cell are significantly enhanced. Thus, when a protein is recombinantly expressed in a microbial host cell, such as e.g. *E coli,* with the peptide tag of the invention fused at the N-terminus, the presence of this tag in most cases enhances expression, due to decreased solubility of the protein and reduced toxicity to the host cell, and it further fulfils a number of additional important criteria required for efficient recombinant protein expression. In particular it allows the protein to be obtained in its mature form after proper cleavage of the tag. Moreover, the alteration of the overall protein charge brought about by the charged tag facilitates the purification of the protein.

EXAMPLES

Example 1

Expression of Tagged Human Interleukin-21

For comparison of various small N-terminal tags, with respect to expression and down-stream processing, the human Interleukin hIL-21 was chosen as the target protein. The nucleic acid molecule encoding the protein Met hIL-21 is given below, where the 5' end and 3' end of the molecule has respectively restriction enzyme sites for Nde1-BamH1.

```
Met hIL-21 Nde1 - BamH1 nucleotide sequence [SEQ ID No: 1]:
CATATGCAAGGTCAAGATCGCCACATGATTAGAATGCGTCAACTTATAGATATTGTTGATCAGCTGAAAA

ATTATGTGAATGACCTGGTTCCGGAATTCCTGCCGGCTCCGGAAGATGTTGAGACCAACTGTGAGTGGTC

CGCTTTCTCCTGTTTCCAGAAAGCCCAGCTGAAATCCGCAAACACCGGTAACAACGAACGTATCATCAAC

GTTTCCATTAAAAAACTGAAACGTAAACCGCCGTCCACCAACGCAGGTCGTCGTCAGAAACACCGTCTGA

CCTGCCCGTCCTGTGATTCTTATGAGAAAAAACCGCCGAAAGAATTCCTGGAACGTTTCAAATCCCTGCT

GCAGAAAATGATTCACCAGCACCTGTCCTCTCGTACCCACGGTTCCGAAGATTCCTGATGATTTGGCGGA

TCC
```

The Met hIL-21 Nde1 - BamH1 nucleotide sequence encodes the Met hIL-21 protein sequence [SEQ ID No: 2]:

```
M - QGQDRHMIRM RQLIDIVDQL KNYVNDLVPE FLPAPEDVET NCEWSAFSCF QKAQLKSANT     60

GNNERIINVS IKKLKRKPPS TNAGRRQKHR LTCPSCDSYE KKPPKEFLER FKSLLQKMIH    120

QHLSSRTHGS EDS
```

A series of constructs were made according to the following scheme:

A 410 base pair DNA molecule, encoding the mature form of hIL-21, corresponding to amino acid residues 1-133 of Met hIL-21, with 5' and 3' end Sty1-BamH1 sites is shown below:

```
hIL-21 Sty1 - BamH1 nucleotide sequence [SEQ ID No: 3]
CCAAGGTCAAGATCGCCACATGATTAGAATGCGTCAACTTATAGATATTGTTGATCAGCTGAAAAATTATG

TGAATGACCTGGTTCCGGAATTCCTGCCGGCTCCGGAAGATGTTGAGACCAACTGTGAGTGGTCCGCTTT

CTCCTGTTTCCAGAAAGCCCAGCTGAAATCCGCAAACACCGGTAACAACGAACGTATCATCAACGTTTCC

ATTAAAAAACTGAAACGTAAACCGCCGTCCACCAACGCAGGTCGTCGTCAGAAACACCGTCTGACCTGCC

CGTCCTGTGATTCTTATGAGAAAAAACCGCCGAAAGAATTCCTGGAACGTTTCAAATCCCTGCTGCAGAA

AATGATTCACCAGCACCTGTCCTCTCGTACCCACGGTTCCGAAGATTCCTGATGATTTGGCGGATCC
```

The hIL-21 Sty1 - BamH1 nucleotide sequence, starting from nucleotide 2, comprises the nucleotide sequence [SEQ ID No: 4],

[SEQ ID No: 4]
```
CAAGGTCAAGATCGCCACATGATTAGAATGCGTCAACTTATAGATATTGTTGATCAGCTGAAAAATTATG

TGAATGACCTGGTTCCGGAATTCCTGCCGGCTCCGGAAGATGTTGAGACCAACTGTGAGTGGTCCGCTTT

CTCCTGTTTCCAGAAAGCCCAGCTGAAATCCGCAAACACCGGTAACAACGAACGTATCATCAACGTTTCC

ATTAAAAAACTGAAACGTAAACCGCCGTCCACCAACGCAGGTCGTCGTCAGAAACACCGTCTGACCTGCC

CGTCCTGTGATTCTTATGAGAAAAAACCGCCGAAAGAATTCCTGGAACGTTTCAAATCCCTGCTGCAGAA

AATGATTCACCAGCACCTGTCCTCTCGTACCCACGGTTCCGAAGATTCCTGATGA
``` which codes for the mature hIL-21 protein sequence having amino acid sequence of SEQ ID No: 5, where * corresponds to a stop codon
[SEQ ID No: 5]:

```
QGQDRHMIRM RQLIDIVDQL KNYVNDLVPE FLPAPEDVET NCEWSAFSCF QKAQLKSANT     60

GNNERIINVS IKKLKRKPPS TNAGRRQKHR LTCPSCDSYE KKPPKEFLER FKSLLQKMIH    120

QHLSSRTHGS EDS*
```

The hIL-21 Sty1-BamH1 molecule was ligated to an Nde1-BamH1 digested T7 expression vector, pET-11 c of 5.6 kb, together with any one of a series of linkers, each flanked by a 5' Nde1 site and a 3' Sty1 compatible site, that are listed below in Table 1:

person skilled in the art to make adjustments to the codons to avoid secondary problems if encountered. Table 1 illustrates two points: The expression levels are generally increased by the addition of the specific peptide tags, and the solubility of hIL-21 is decreased thereby protecting the E. coli host cell

TABLE 1

| Name of construct | Amino acid sequence of tag | Expression level | DNA sequence of tag* |
|---|---|---|---|
| Met hIL-21 | (M) | 1-2 | No tag |
| DAP 14 | MHAH [SEQ ID No: 6] | 1 | 5'T ATG CAT GCG CAT 3' [SEQ ID No:17]<br>AC GTA CGC GTA GTT C |
| DAP 25 | MHAH [SEQ ID No: 7] | 4-5 | 5'T ATG CAC GCT CAC 3' [SEQ ID No:18]<br>AC GTG CGA GTG GTT C |
| DAP 15 | MHHA [SEQ ID No: 8] | 4 | 5'T ATG CAT CAC GCG 3' [SEQ ID No:19]<br>AC GTA GTG CGC GTT C |
| DAP 16 | MHHQ [SEQ ID No: 9] | 3-4 | 5'T ATG CAT CAC CAG 3' [SEQ ID No:20]<br>AC GTA GTG GTC GTT C |
| DAP 22 | MHHV [SEQ ID No:10] | 4 | 5'T ATG CAT CAC GTG 3' [SEQ ID No:21]<br>AC GTA GTG CAC GTT C |
| DAP 17 | MKHK [SEQ ID No:11] | 4 | 5'T ATG AAA CAC AAA 3' [SEQ ID No:22]<br>AC TTT GTG TTT GTT C |
| DAP 18 | MKAK [SEQ ID No:12] | 2-3 | 5'T ATG AAA GCG AAA 3' [SEQ ID No:23]<br>AC TTT CGC TTT GTT C |
| DAP 19 | MRAR [SEQ ID No:13] | 3 | 5'T ATG CGT GCG CGT 3' [SEQ ID No:24]<br>AC GCA CGC GCA GTT C |
| DAP 21 | MKMK [SEQ ID No:14] | 4 | 5'T ATG AAA ATG AAA 3' [SEQ ID No:25]<br>AC TTT TAC TTT GTT C |
| DAP 23 | MKSK [SEQ ID No:15] | 6 | 5'T ATG AAA AGC AAA 3' [SEQ ID No:26]<br>AC TTT TCG TTT GTT C |
| DAP 24 | MKTK [SEQ ID No:16] | 4 | 5'T ATG AAA ACC AAA 3' [SEQ ID No:27]<br>AC TTT TGG TTT GTT C |

The T7 expression vector, pET-11 c, comprising a linker containing a DNA tag, ligated in-frame to the DNA molecule, hIL-21 Sty1-BamH1 was transformed into the host cell E. coli B BL21 (DE3).

Host cell strains, transformed with each of the T7 expression vectors, were grown at 37° C. in LB medium, supplemented with ampicillin 0.2 mg/l, and recombinant protein expression from the T7 expression vector was induced with 0.5 mM IPTG for 3-4 hours. The host cells were then harvested by centrifugation, lysed and then the sample was centrifuged to provide a soluble fraction and a pelleted inclusion body fraction. The total cell extract, the inclusion body and soluble cell fraction from each host cell sample was then separated by SDS PAGE, and the gels were stained with Comassie blue to determine the relative level of tagged hIL-21 protein expression, as compared with the untagged protein, Met hIL-21.

The expression level of the various tagged versions of hIL-21 is dependant on the amino acid sequence of the tag, as shown in Table 1, but it is also in some cases dependant on the nucleotide sequence, as can be seen from DAP 14 and DAP 25 with identical amino acid sequences. In DAP 14, the low expression level is most likely due to the formation of a loop structure, i.e. secondary structure, in the mRNA in the region of translation start, while changing 3 of the codons in DAP 25 leads to a more open structure. It is within the skills of a from the poisonous effects of hIL-21. Also, the decrease in solubility favors the partitioning of hIL-21 into inclusion bodies and thereby facilitates its subsequent purification.

Example 2

Figure 1:
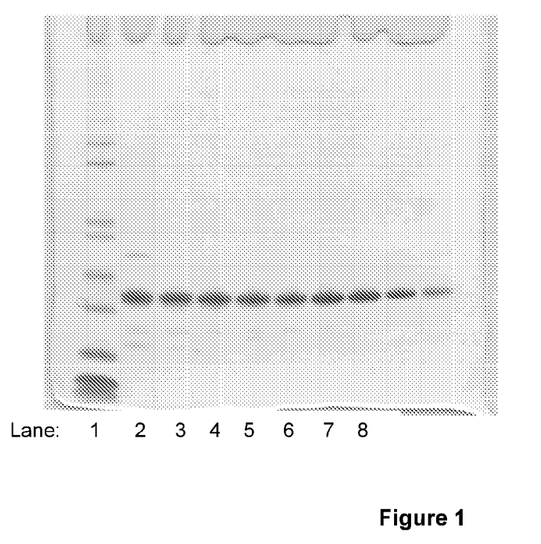
FIG. 1: SDS-polyacrylamide gel, stained with coomassie-blue showing sepharose SP column fractions sampled during purification of recombinantly expressed MKHK-hIL-21: lane 1; protein molecular weight markers; lanes 2-10 are fractions from Sepharose SP column.

Recombinantly Expressed Tagged Human Interleukin-21 is Processed to Its Mature and Active Form MKHK-hIL-21, expressed using construct DAP17, was refolded from inclusion bodies as disclosed in WO 04/55168 and subsequently purified to approximately 90-95% purity employing Sepharose SP column chromatography. A single major polypeptide band corresponding to MKHK-hIL-21 was detected by SDS-PAGE analysis of fractions obtained from the Sepharose SP column, as seen in FIG. 1, lanes 2-10. Pools of fractions, shown in lanes 4-10, were subsequently subjected to dipeptidyl aminopeptidase (DAPase) and glutamine cyclotransferase (Q cyclase) treatment in order to perform a controlled removal of the N-terminal peptide tag of four amino acids. The conditions for peptide tag cleavage were: an aqueous solution of 27.5 μM MKHK-IL21, 67.5 mU DAPase, 5.5 U Q cyclase, 25 mM Tris, 0.15 M NaCl, pH 7.0, incubated for 90 minutes at ambient temperature (20-25° C.), employing enzymes supplied by Qiagen.com.

Figure 2:
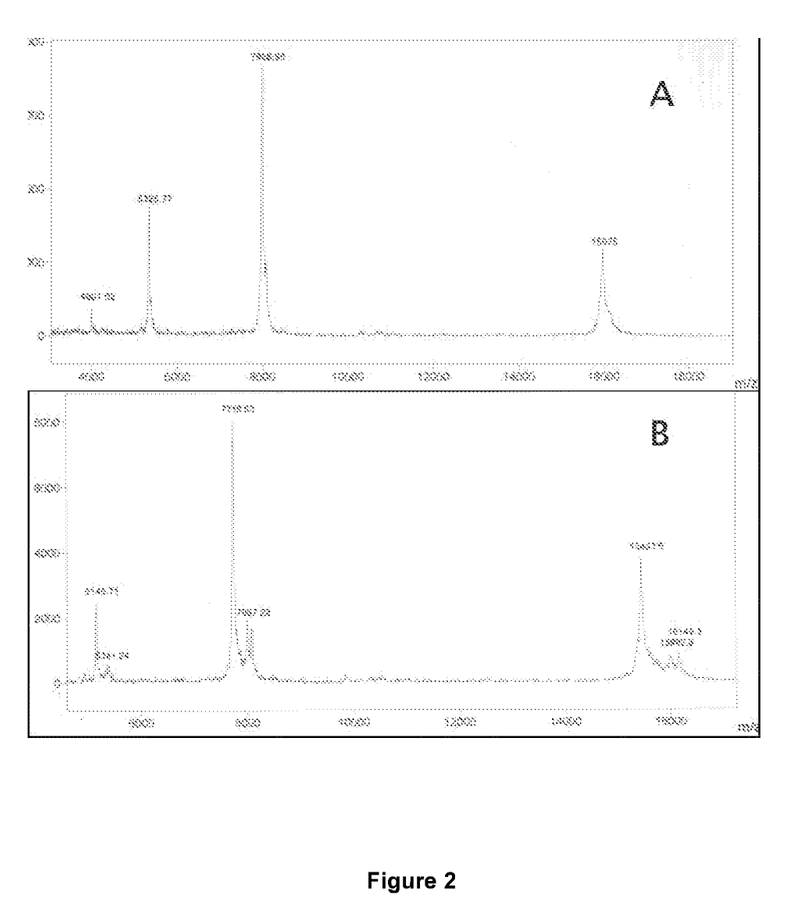
FIG. 2: The efficiency and completion of tag removal to yield mature hIL-21 was determined by mass spectrometry, as shown in FIG. 2, A and B.

The efficiency and completion of tag removal to yield mature hIL-21 was determined by mass spectrometry, as shown in FIG. 2, A and B.

Panel A shows the Maldi spectrum of fractions prior to tag removal

Panel B shows the same fractions after tag removal.

Native hIL21 have a molecular weight of 15433 Da, while the MKHK-IL21 has a molecular weight of 15975 Da. As observed in panel B, cleavage and tag removal was approximately 90% complete.

Biological activity as tested in a BaF assay (assay 1) using the IL-21 receptor showed that the potency of the cleaved native IL-21 was equipotent to Met-IL21 produced by 10 the methods described in WO 04/55168.

PHARMACOLOGICAL METHODS

Assay (I) BAF-3 assay to determine IL-21 activity

The BAF-3 cells (a murine pro-B lymphoid cell line derived from the bone marrow) was originally IL-3 dependent for growth and survival. Il-3 activates JAK-2 and STAT which are the same mediators IL-21 is activating upon stimulation. After transfection of the human IL-21 receptor the cell line was turn into a IL-21-dependent cell line. This clone can be used to evaluate the effect of IL-21 samples on the survival of the BAF-3 cells.

The BAF-3 cells are grown in starvation medium (culture medium without IL-21) for 24 hours at 37° C., 5% $CQ_2$.

The cells are washed and re-suspended in starvation medium and seeded in plates. 10 µl of IL-21 compound, human IL-21 in different concentrations or control is added to the cells, and the plates are incubated for 68 hours at 37° C., 5% $CQ_2$.

AlamarBlue® is added to each well and the cells are then incubated for another 4 hours. The AlamarBlue® is a redox indicator, and is reduced by reactions innate to cellular metabolism and, therefore, provides an indirect measure of viable cell number.

Finally, the metabolic activity of the cells is measure in a fluorescence plate reader. The absorbance in the samples is expressed in % of cells not stimulated with growth hormone compound or control and from the concentration-response curves the activity (amount of a compound that stimulates the cells with 50%) can be calculated.

The invention claimed is:

1. A tagged protein comprising an N-terminal peptide tag fused to a protein, wherein said peptide tag consisting of the amino acid sequence set forth in SEQ ID Nos: 7, 8, 9, 10, 11, 12, 13, 14, 15 or 16.

2. The tagged protein of claim 1, wherein said peptide tag consisting of the amino acid sequence set forth in SEQ ID No: 7, 8, 10, 11, 14, 15 or 16.

3. The tagged protein of claim 2, wherein said peptide tag consisting of the amino acid sequence of SEQ ID No: 15.

4. The tagged protein of claim 1, wherein said protein has an amino acid sequence of SEQ ID No: 5.

* * * * *